(12) United States Patent
Shirley et al.

(10) Patent No.: US 6,306,432 B1
(45) Date of Patent: *Oct. 23, 2001

(54) HIGH AND LOW LOAD FORMULATIONS OF IGF-I IN MULTIVESICULAR LIPOSOMES

(75) Inventors: Bret Shirley, Concord; Maninder Hora, Danville; Qiang Ye, San Diego; Nandini Katre, Solana Beach; John Asherman, San Diego, all of CA (US)

(73) Assignees: Chiron Corporation, Emeryville; SkyePharma Inc., San Diego, both of CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/925,531

(22) Filed: Sep. 8, 1997

(51) Int. Cl.[7] .................................. A61K 9/127
(52) U.S. Cl. ..................... 424/450; 264/4.1; 264/4.3; 514/3; 514/21
(58) Field of Search .................. 424/450, 1.21, 424/9.321, 9.51, 417; 264/4.1, 4.3; 436/829; 935/54; 514/3, 21

(56) References Cited

U.S. PATENT DOCUMENTS

Re. 35,192   3/1996   Reese .
4,078,052    3/1978   Papahadjopoulous .

(List continued on next page.)

FOREIGN PATENT DOCUMENTS 2050287      1/1981   (GB) .

OTHER PUBLICATIONS

Katre, N.V. et al., A Multivesicular Lipid–Based Sustained–Release System for the Delivery of Therapeutic Proteins. *Abstract for the 8th International Pharmaceutical Technology Symposium on Recent Advances in Peptide and Protein Delivery* Sep. 9–11, 1996, Ankara, Turkey.

Huang, "Studies on Phosphatidylcholine Vesicles Formation and Physical Characteristics," *Biochemistry*, 8:334–352, 1969.

Bangham, "Diffusion of Univalent Ions Across The Lamellae of Swollen Phospholipids," *J. Mol. Bio.*, 13:238–252, 1965.

Szoka, et al., Comparative Properties and Methods of Preparation of Lipid Vesicles (Liposomes), *Ann. Rev. Biophys. Bioengineering*, 9:467–508, 1980.

(List continued on next page.)

Primary Examiner—Gollamudi S. Kishore
(74) Attorney, Agent, or Firm—Fish & Richardson P.C.

(57) ABSTRACT

Disclosed are multivesicular liposomes (MVLs) containing IGF-I with substantially full bioavailability, wherein the loading of the IGF-I into the liposomes is modulated by adjusting the osmolarity of the aqueous component into which the agents are dissolved prior to encapsulation. In the making of MVLs, the process involves dissolving the IGF-I, an osmolarity excipient, and a pH modifying agent sufficient to solubilize the IGF-I in a first aqueous component used during manufacture of the MVLs. To increase the loading of the IGF-I, the osmolarity of the aqueous component used during manufacture of the MVLs is reduced, whereas the osmolarity of the aqueous component is increased to obtain the low load formulations. The rate of release of the active agent into the surrounding environment in which the liposomes are introduced can be simultaneously controlled by incorporating into the lipid component used in the formulation at least one long chain amphipathic lipid. Use of the long chain amphipathic lipid in the lipid component is particularly helpful in controlling the release rate from high drug load formulations.

42 Claims, 6 Drawing Sheets

U.S. PATENT DOCUMENTS

| | | |
|---|---|---|
| 4,089,801 | 5/1978 | Schneider . |
| 4,145,410 | 3/1979 | Sears . |
| 4,224,179 | 9/1980 | Schneider . |
| 4,235,871 | 11/1980 | Papahadjopoulos et al. . |
| 4,310,506 | 1/1982 | Baldeschwieler et al. . |
| 4,394,372 | 7/1983 | Taylor . |
| 4,522,803 | 6/1985 | Lenk et al. . |
| 4,588,578 | 5/1986 | Fountain et al. . |
| 4,599,227 | 7/1986 | Dees et al. . |
| 4,610,868 | 9/1986 | Fountain et al. . |
| 4,752,425 | 6/1988 | Martin et al. . |
| 4,769,250 | 9/1988 | Forseen . |
| 4,781,871 | 11/1988 | West, III et al. . |
| 4,920,016 | 4/1990 | Allen et al. . |
| 4,921,853 | 5/1990 | LeBlanc . |
| 5,000,959 | 3/1991 | Iga et al. . |
| 5,021,200 | 6/1991 | Vanlerberghe et al. . |
| 5,077,056 | 12/1991 | Bally et al. . |
| 5,091,187 | 2/1992 | Hayes . |
| 5,173,219 * | 12/1992 | Kim ........................................ 264/4.6 |
| 5,204,112 | 4/1993 | Hope et al. . |
| 5,206,023 * | 4/1993 | Hunziker .............................. 424/423 |
| 5,211,955 | 5/1993 | Legros et al. . |
| 5,227,165 | 7/1993 | Domb et al. . |
| 5,244,678 | 9/1993 | Legros et al. . |
| 5,246,707 | 9/1993 | Haynes . |
| 5,261,903 | 11/1993 | Dhaliwal et al. . |
| 5,321,012 | 6/1994 | Mayer et al. ........................... 514/25 |
| 5,334,381 | 8/1994 | Unger . |
| 5,334,391 | 8/1994 | Clark et al. . |
| 5,422,120 * | 6/1995 | Kim ...................................... 424/450 |
| 5,451,408 | 9/1995 | Mezei et al. . |
| 5,723,147 * | 3/1998 | Kim ...................................... 424/450 |
| 5,766,027 * | 6/1998 | Sankaram .............................. 424/450 |

OTHER PUBLICATIONS

Shakiba, et al., "Evaluation of Retinal Toxicity and Liposome Encapsulation of the Anti–CMV Drug 2'–nor–cyclic CMP," *Investigative Ophthalmology and Visual Science*, No. 10, 34:2903–2910, Sep. 1993.

Frucht–Perry, et al., "Fibrin–Enmeshed Tobramycin Liposomes: Single Application Topical Therapy of . . . ," *Cornea*, No. 5, 11:393–397, Sep. 1992.

Assil, et al., "Tobramycin Liposomes. Single Subconjunctival Therapy of . . . ," *Investigative Ophthalmology and Visual Science*, No. 13, 32:3216–3220, Dec. 1991.

Assil, et al., "Liposome Suppression of Proliferative Vitreoretinopathy. Rabbit . . . ," *Investigative Ophthalmology and Visual Science*, No. 13, 32:2891–2897, Oct. 1991.

Turski, et al., "Magnetic Resonance Imaging of Rabbit Brain After Intracarotid Injection . . . ," *Magnetic Resonance in Medicine*, No. 2, 7:184–196, Jun. 1998.

Skuta, et al., "Filtering Surgery in Owl Monkeys Treated With the Antimetabolite . . . ," *American Journal of Ophthalmology*, No. 5, 103:714–716, May 15, 1987.

Assil, et al., "Multivascular Liposomes. Sustained Release of the Anitmetabolite . . . ," *Archives of Ophthalmology*, No. 3, 105:400–403, Mar., 1987.

Barbet, et al., "Weak Acid–Induced Release of Liposome–Encapsulated Carboxyfluorescein," *Biochimica et Biophysica Acta*, No. 3, 772:347–356, May 30, 1984.

Kim, et al., "Preparation of Cell–Size Unilamellar Liposomes with High Captured Volume and Defined Size . . . ," *Biochim. Biophys. Acta*, 646:1–9, 1981.

Kim et al., "Preparation of Multivesicular Liposomes," *Biochim. Biophys. Acta*, 728: 339–348, 1983.

Kim, et al., "Preparation of Multilamellar Vesicles of Defined Size–Distribution by Solvent–Spherule . . . ," *Biochim. Biophys. Acta*, 812: 793–801, 1985.

Kim, et al., "Multivescular Liposomes Containing Entrapped in the Presence of . . . ," *Cancer Treat. Rep.*, 71: 705–711, 1987.

Kim, et al., "Multivesicular Liposomes Containing Cytosine 1–β–D–Arabinofuranosylcytosine for Slow–Release Intrathecal Therapy," *Cancer Treat. Rep.*, 47: 3935–3937, 1987.

Kim, et al., "Multivesicular Liposomes Containing for Slow Release . . . ," *Cancer Treat. Rep.*, 71: 447–450 1987.

Kim, et al., "Modulation of the Peritoneal Clearance of Liposomal Cytosine Arabinoside by . . . ," *Cancer Chemother. Pharmacology*, 19:307–310, 1987.

Roy, et al., "Multivesicular Liposomes Containing Blemomycin for Subcutaneous Administration," *Cancer Chemother. Pharmacology*, 28: 105–108, 1991.

Kim, et al., "Prolongation of Drug Exposurein Cerebrospinal Fluid by Encapsulation Into . . . ," *Camcer Chemother. Pharmacology*, 55: 1596–1598, Apr. 1, 1993.

Kim, et al., "Driect Cerebrospinal Fluid Delivery of an Antiretroviral Agent Using . . . ," *Jrnl. Of Infectious Diseases.*, 162: 750–752, 1990.

* cited by examiner

Figure 2: *In vitro* plasma release characteristics of IGF-I encapsulated in multivesicular liposomes. These three formulations correspond to those presented in Table 6E: (A) open diamond; (B) open triagle; and (C) cross, with error bars representing S.D. The data indicate a sustained release of IGF-I.

Figure 3 *In vivo* pharmacokinetics of multivesicular liposome encapsulated IGF-I (formulation A in Table 6E) after a subcutaneous injection of 10 mg dose into male rats. The data (mean of three rats) demonstrate a sustained release of IGF-I over a week period.

HIGH AND LOW LOAD FORMULATIONS OF IGF-I IN MULTIVESICULAR LIPOSOMES

BACKGROUND OF THE INVENTION

1. Field of the Invention

The present invention relates to slow release vehicles for delivering a biologically active agent. More particularly, the present invention relates to multivesicular liposomes containing IGF-I.

2. Description of Related Art

Proteins which are cleared rapidly from the circulation after intravenous or subcutaneous injections need to be administered repeatedly in order to maintain therapeutic blood levels. One of the proteins that needs frequent administration for therapeutic benefit is Insulin-like Growth Factor I (IGF-I). Mature, circulating IGF-I, a 7.65 kD protein, consists of B and A domains (homologous to the B and A chains of insulin). Unlike insulin, the B and A domains of the IGFs are connected by a C peptide, and contain an eight-amino-acid extension at the C-terminus, termed the D domain.

Native IGF-I contains three disulfide bonds involving the following residues: CysB6–CysB7, CysA6–CysA11, and CysB18–CysA20. Under reducing conditions, these disulfide bonds are broken and can become "scrambled" during oxidative refolding in denaturant solutions to yield two alternative disulfide isomers with distinct tertiary structures (L. O. Narhi et al., *Biochemistry* 32/5214–5221, 1993).

IGF-I is known to have multiple biological activities. Those with therapeutic potential are its activity in reversing catabolism in states of starvation, severe illness, or injury, in enhancing wound healing and nerve regeneration, and in reducing insulin resistance in diabetics. IGF-I is also known to generally stimulate the growth and maintenance of nervous tissue, increase glucose uptake of cells, and stimulate renal function. Chronic malnutrition and poorly controlled diabetes in the young are associated with lower circulating IGF-I levels and growth retardation.

Optimal treatment with IGF-I may require that the drug level be maintained at a specified level for a prolonged period of time. For example, optimal treatment of insulin dependency in diabetics may require maintenance of a relatively high level of IGF-I for a period of several days.

For certain other therapeutic usages, for example treatment of malnutrition or osteoporosis, a low level of IGF-I released over a period of several days would be beneficial.

One approach which has been used to provide controlled release compositions for drug delivery is liposome encapsulation. Among the main types of liposomes, multivesicular liposomes (Kim, et al., *Biochim. Biophys. Acta;* 728:339–348, 1983), are uniquely different from unilamellar liposomes (Huang, *Biochemistry;* 8:334–352, 1969; Kim, et al., *Biochim. Biophys. Acta;* 646:1–10, 1981), multilamellar liposomes (Bangham, et al, *J. Mol. Bio.,* 13:238–252, 1965), and stable plurilamellar liposomes (U.S. Pat. No. 4,522, 803). In contrast to unilamellar liposomes, multivesicular liposomes contain multiple aqueous chambers. In contrast to multilamellar liposomes, the multiple aqueous chambers of multivesicular liposomes are non-concentric with membrane distributed as a network throughout.

In multivesicular liposomes the encapsulation efficiency of some small molecules, such as cytosine arabinoside, is relatively low, and the release rate of encapsulated molecules in biological fluids is faster than is therapeutically desirable unless the osmolarity of the first aqueous component is adjusted to control the rate of release. EP 0 280 503 B1 discloses coencapsulation of a hydrochloride such as hydrochloric acid, with an active agent to control the rate of release of the active agent. Further research, disclosed in WO 95/13796, has shown that the release rate of agents from multivesicular liposomes in human plasma can also be controlled by introduction of a non-hydrochloride acid into the aqueous solution in which the agent is dissolved prior to forming the multivesicular liposome. It is also known (WO 96/08253) to control the rate of release of active agents by introducing other types of solutes called "osmotic spacers" into the aqueous solution in which the active agent is dissolved prior to formation of the multivesicular liposomes.

In addition to the biologically active agent and acids or osmotic spacers intended to control the rate of release of the biologically active agent from the liposomes, it is common practice to coencapsulate with the active agent compounds that are intended to serve any of a number of helper functions. For instance, certain biologically active compounds retain activity only when kept at a particular pH. Thus acids or buffers are often necessarily encapsulated in addition to the active agent to control the pH of the drug environment. In other cases, a counterion is incorporated to enhance solubility of a biologically active agent that has low solubility.

Thus the need exists for new high load and low load slow release formulations of IGF-I having the bioactivity of free drug in a vehicle suitable as a slow release drug depot. Since IGF-I is an expensive drug, whether purified from biological samples or produced recombinantly, a need also exists to achieve these goals while keeping the encapsulation efficiency as high as possible to avoid waste of the expensive active agents.

SUMMARY OF THE INVENTION

The present invention provides a method for obtaining high loading and low loading formulations of IGF-I in multivesicular liposomes (MVLs) in an aqueous suspending medium and MVL formulations containing them. The low loading formulations are obtained by utilizing during manufacture a first aqueous component comprising a concentration of dissolved IGF-I from about 1 mg/mL to about 33 mg/mL, for example, about 5 mg/mL to about 20 mg/mL. The first aqueous component used in making the low loading formulations further can contain one or more osmotic excipients, such as sucrose, and sufficient of one or more pH adjusting agent, such as ammonium citrate dibasic, to maintain the pH in the range from about 1 to about 5.

The high loading formulations generally are obtained by utilizing during manufacture a first aqueous component containing a concentration of dissolved IGF-I from about 40 mg/mL to about 300 mg/mL, for example from about 100 mg/mL to about 160 mg/mL. The first aqueous component in the high load formulation further contain an acid, such as citric acid, sufficient to maintain the pH in the range from about 2 to about 4.8, and an osmotic excipient, such as sucrose.

Both the high load and low load formulations can be further diluted by addition of suspending medium or other biologically acceptable carrier to obtain injectable or implantable slow release depot formulations of any therapeutically effective total dosage.

Methods for making MVLs are well known in the art and are described in U.S. Pat. Nos. 5,455,044, 5,576,018, and in copending U.S. patent application Ser. Nos. 08/305,158, filed Apr. 13, 1994; 08/473,019, filed Jun. 6, 1995; 08/473, 013, filed Jun. 6, 1995 and 08/502,569, filed Jul. 14, 1995. all of which are incorporated herein by reference in their entireties. The general procedure for making multivesicular liposomes imparts to them their characteristic properties, including the properties of modulated release of encapsulated biologically active substances. In this method, a "water-in-oil" emulsion containing the biologically active substance to be encapsulated is first made by dissolving at least one amphipathic lipid and at least one neutral lipid in a volatile organic solvent for the lipid component, adding to the lipid component an immiscible first aqueous component and emulsifying the mixture. A hydrochloride or non-hydrochloride acid can be added to either or both of the first aqueous component and the lipid component to control release of the active agent from the MVLs. In this general method, the biologically active substance to be encapsulated can be contained in the first aqueous component or in the lipid component, or both.

The entire water-in-oil emulsion is then mixed with the second aqueous component, and agitated mechanically, as above, to form solvent spherules suspended in the second aqueous component. The solvent spherules contain multiple aqueous droplets with the substance to be encapsulated dissolved therein. In the final step, the volatile organic solvent is removed from the spherules, for instance by evaporation. When the solvent is completely removed, multivesicular liposomes are formed. Representative gases satisfactory for use in evaporating the solvent include nitrogen, helium, argon, oxygen, hydrogen and carbon dioxide. Alternatively, the organic solvent can be removed by sparging, rotary evaporation, or solvent selective membranes. The multivesicular liposome particles are then suspended in an aqueous medium for storage and use.

In the present invention, this general procedure is modified in certain key instances to obtain the high load and low load MVL formulations of IGF-I. In particular, the composition of the first aqueous component is modulated to control loading of the IGF-I in the final product. Further, the IGF-I is dissolved in the first aqueous component, rather than being dissolved in the lipid component, and, of greater importance, the osmolarity of the aqueous component into which the active agent is dissolved for encapsulation is adjusted to control loading of the biologically active agent, therein.

An inverse relation between osmolarity and drug loading has been discovered, with the loading of IGF-I increasing as the osmolarity of the aqueous component used during manufacture of MVLs decreases and vice versa. Thus, the key parameter that is manipulated in making MVLs with either high or low loading of IGF-I is the osmolarity of the drug-containing first aqueous solution used during the process of manufacture. In the present invention, the osmolarity of the aqueous solution is adjusted by dissolving an osmotic excipient, such as sucrose or glycylglycine, therein, with a higher concentration of osmotic excipient leading to a lower loading of the active agent, and vice versa. When sucrose is used as an osmotic excipient, for the low load formulations, the concentration of sucrose in the first aqueous component during manufacture is about 5 to about 7 percent on a weight by volume basis (% w/v), while for the high load formulations, the concentration of sucrose is in the range from zero to about 2.5 percent on a weight by volume basis.

Applicants have also discovered a second parameter that must be taken into consideration in determining the composition of the first aqueous component during manufacture of the IGF-I formulations of this invention. The concentration of IGF-I in solution in the first aqueous component during manufacture is directly proportional to the amount of IGF-I that can be loaded in any give formulation. However, the solubility of IGF-I in aqueous solution drops precipitously at a pH of about 5. FIG. 1 shows the solubility of about 120 mg/mL concentration of IGF-I in 20 mM ammonium citrate in 5 weight by volume percent sucrose in the pH range from 4.5 to 5.5. Further studies have shown that up to about 300 mg/mL of IGF-I can be solubilized at a pH below 5. Thus, to obtain and maintain sufficient IGF-I in solution in the first aqueous solution, a buffer or acid is also added to it during manufacture to assure a high enough concentration of dissolved IGF-I in the first aqueous component to obtain a final MVL product containing the desired loading of the drug. For the low load formulations, the pH of the first aqueous component is generally adjusted to a value within the range of 1 to about 5, while for high load formulations the pH range is between 2 and 4.8.

Since all solutes in the first aqueous solution, including the buffer, or other pH adjusting agent, contribute to its osmolarity, the amount of the osmotic excipient and pH adjusting agent must be balanced to maintain solubility of the drug in the final product while allowing for loading of the desired concentration of the drug. As one skilled in the art will appreciate, some portion of the osmotic excipients, including the buffer will pass through the permeable vesicle membranes, so the osmolarity of aqueous component in the final product is not generally the same as the osmolarity of the first aqueous component used at the time of manufacture.

In one embodiment of the invention, low load IGF-I MVL formulations are obtained by using a first aqueous component that contains from about 9 mg/mL to about 16 mg/mL of IGF-I, 3 to 7 % w/v of sucrose as osmotic excipient, and 20 mM ammonium citrate dibasic pH 4.5–5.5 as a buffer to maintain the pH of the aqueous component in the range necessary to assure that the IGF-I will remain in solution, but without risk of denaturing the protein. The corresponding osmolarity of the first aqueous component is in the range from about 130 to about 290 mOsm. In another embodiment, in the pH range from about 1 to about 5, when the concentration of IGF-I is in the range from about 1 mg/mL to about 33 mg/mL, the first aqueous component contains sufficient of an osmotic excipient to bring its osmolarity within the range from about 160 mOsm to about 320 mOsm. In all cases the lower end of the osmolarity range corresponds to the upper end of the drug concentration range.

The high load MVL formulations of IGF-I are obtained by using a first aqueous component during manufacture that comprises from about 40 to about 300 mg/mL, for example, about 20 to about 80 mg/mL of IGF-I, sufficient of a pH adjusting agent to keep the pH in the range from about 2 to about 4.8, and sufficient of an osmotic excipient to bring the osmolarity within the range from about 5 to about 150 mOsm, with the lower end of the osmolarity range corresponding to the higher end of the drug concentration range. In one embodiment, the osmotic excipient is from zero to about 2.5 weight by volume percent of sucrose and 25 mM citric acid is used as the pH adjusting agent.

To maintain a high encapsulation efficiency (or percent yield) during formulation of the MVLs and ensure that release of the active agent in use is at a slow therapeutically effective rate, the lipid component contains one or more amphipathic lipid having from about 13 to about 28, for example, about 18 to 22 carbons in its carbon chain.

In another embodiment, a high load multivesicular liposome formulation containing from about 50 mg/mL to about 80 mg/mL of IGF-I is provided. The formulation comprises an aqueous suspension of a multivesicular liposome comprising IGF-I in an aqueous component, an amphipathic lipid containing from about 18 to 22 carbons in the carbon chain; and a neutral lipid lacking a hydrophilic head group. The formulation can contain less than 2 percent of the IGF-I in the aqueous suspension on a weight by volume basis.

Pharmaceutical compositions are also provided which comprise a multivesicular liposome made by the method of this invention, wherein the suspending medium further comprises a physiologically acceptable carrier, and the total amount of the IGF-I in the composition is a therapeutically effective dosage.

DESCRIPTION OF PREFERRED EMBODIMENTS

Figure 1:
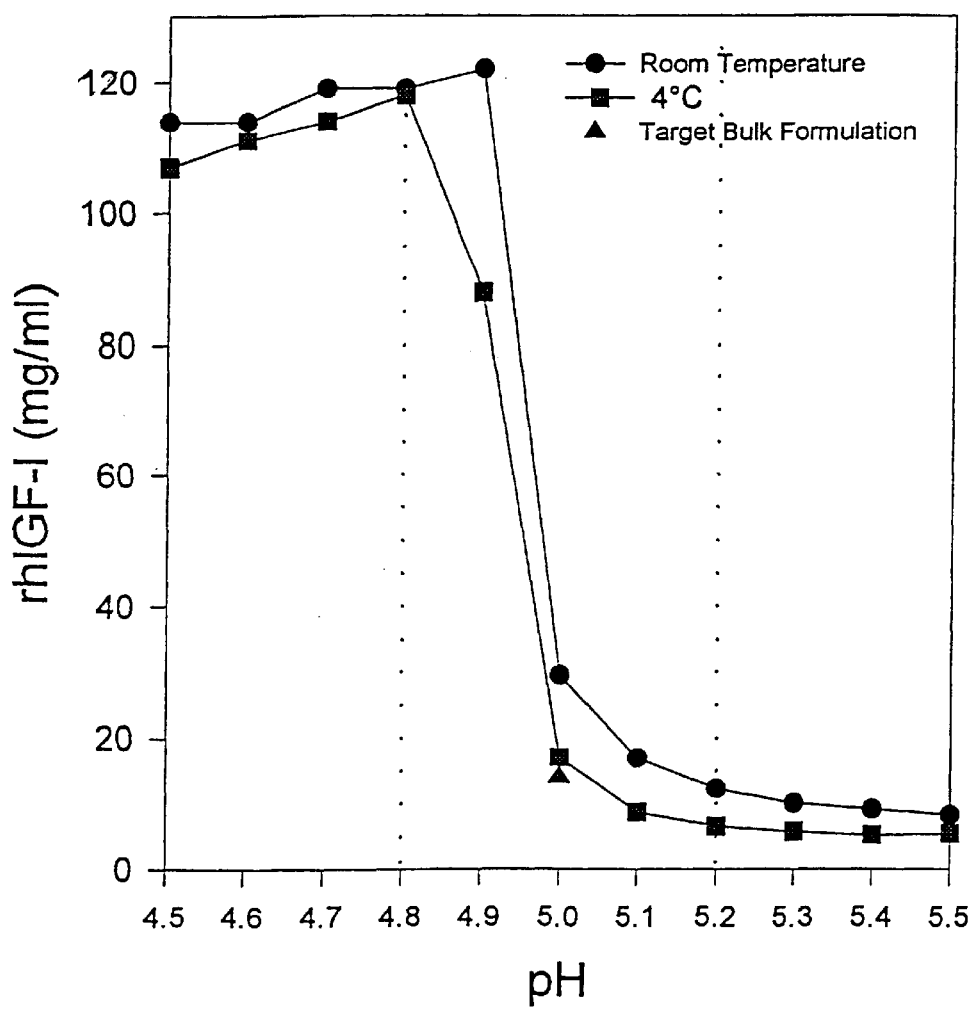
FIG. 1 is a graph showing the percent of IGF-I retained in high load MVLs incubated in vitro in plasma at 37° C. over 7 days (rate of release). Various concentrations of IGF-I and an osmotic excipient were used in the first aqueous component used during manufacture to control drug loading. ◇=80 mg/mL IGF-I in 25 mM citric acid, and 2.5 w/v % sucrose (113.5 mOsm); ▽=80 mg/mL IGF-I in 25 mm citric acid, 1 w/v % glycylglycine (113.5 mOsm); +=50 mg/mL IGF-I in 25 mm citric acid, 1 w/v % sucrose (63.5 mOsm). Error bars represent standard deviation.

It has been discovered that modulation of IGF-I loading in multivesicular liposomes (MVLs), particularly to achieve high drug loading, can be accomplished without sacrifice of either high encapsulation efficiency in the method of manufacture or desirable controlled release of drug from the final product in use. Drug loading in MVLs is modulated by controlling the osmolarity of the first aqueous component used during manufacture of the MVLs. Osmolarity is the sum of the molar concentrations of solutes present in an aqueous solution. If the solute is present in a dissociated, ionized or aggregated form, osmolarity is defined as the sum of the molar concentrations of the dissociated, ionized or aggregated forms. The solutes that contribute to the osmolarity of an aqueous solution include the IGF-I, and osmotic excipients that are to be encapsulated during manufacture of MVLs. The contribution to the osmolarity of a solution made by any solute in the solution is approximately equivalent to the weight concentration of the solute in the solution (e.g., mg/mL) divided by its molecular weight. Thus, as a general principle, for a given weight concentration, the larger the molecular weight of a solute, the smaller the osmolarity of the solute, and the smaller the contribution of that solute to the overall osmolarity of the solution. It is also possible to reduce the osmolarity of the first aqueous component by reducing the concentration of the active agent. This method will lead to a lower loading of IGF-I if the concentration of other solutes in the first aqueous component remain constant.

Drug loading is the concentration of drug per unit of encapsulated volume of liposomes. An inverse correlation has been discovered between the osmolarity of the first aqueous solution used in manufacture of MVL, and the amount of IGF-I that can be loaded into the vesicles. Therefore, solutes other than IGF-I present in the first aqueous solution used during manufacture of the liposomes tend to reduce the amount of IGF-I that can be loaded into the liposomes. To accommodate this discovery, in the present invention the beneficial effects of the helper osmotic excipients, such as the buffer used to maintain solubility of the IGF-I during manufacture and in the product MVLs, must be balanced against the adverse effect upon drug loading attributable to the osmotic excipients. This problem is particularly acute in making of high loading formulations.

In the Examples herein, the inverse effect of osmolarity on drug loading (i.e. drug encapsulation per unit of encapsulated volume) and the method of modulating drug loading by adjusting the osmolarity of the drug-containing aqueous solution before encapsulation has been illustrated in both high load and low load MVL formulations of IGF-I. The results of these studies show that MVL formulations can be produced having a broad range of loading of IGF-I.

In manufacture of multivesicular liposomes having controlled loading of IGF-I, osmolarity of the first aqueous solution is adjusted to obtain a therapeutically effective level of drug loading for an intended use as follows. A lipid component containing at least one amphipathic lipid and one neutral lipid dissolved in one or more organic solvents is mixed with an immiscible first aqueous component. The first aqueous component contains the IGF-I, an optional osmotic excipient, and a pH adjusting amount of an acid or buffer. In one embodiment, in the high load formulations, the buffer is citric acid, generally 25 mM citric acid, while in the low load formulations the buffer is ammonium citrate dibasic, generally, 20 mM ammonium citrate dibasic, adjusted to about pH 5 with citric acid. The loading of the active agent in the final formulation depends upon the concentration of dissolved drug as well as the overall osmolarity of this first aqueous component, which is the sum of the osmolarity contributed by each of the solutes dissolved in the first aqueous component, including the IGF-I, the osmotic excipient, and the pH adjusting agent.

Once the osmolarity of the first aqueous component has been adjusted to achieve the desired loading of the active agent in the final product, a water-in-oil emulsion is formed by mixing of the two immiscible components. The water-in-oil emulsion is then mixed into a second immiscible aqueous component to form solvent spherules. The organic solvent is finally removed from the solvent spherules, for example by evaporation, to cause them to aggregate into MVLs. In the final step of the process, the MVLs are suspended in an aqueous medium, such as normal saline. The overall amount of active agent in the formulation on a weight by volume of formulation basis can be adjusted to any desired level by increasing or decreasing the volume of the medium in which the MVLs are suspended.

There are at least three types of liposomes. The term "multivesicular liposomes (MVL)" as used throughout the specification and claims means man-made, microscopic lipid vesicles comprising lipid membranes enclosing multiple non-concentric aqueous chambers with membranes distributed as a network throughout. (See Kim et al., *Biochem. Biophys. Acta,* 728:339–348, 1983).

The term "solvent spherule" as used throughout the specification and claims means a microscopic spheroid droplet of organic solvent, within which are multiple smaller droplets of aqueous solution. The solvent spherules are suspended and totally immersed in a second aqueous solution.

The term "neutral lipid" means an oil or fat that has no membrane-forming capability by itself and lacks a hydrophilic "head" group.

The term "amphipathic lipid" means a molecule that has a hydrophilic "head" group and hydrophobic "tail" group and has membrane-forming capability.

The term "zwitterionic lipid" means an amphipathic lipid with a net charge of zero at pH 7.4.

The term "anionic lipid" means an amphipathic lipid with a net negative charge at pH 7.4.

The term "cationic lipid" means an amphipathic lipid with a net positive charge at pH 7.4.

For making multivesicular liposomes, it is required that at least one amphipathic lipid and one neutral lipid be included in the lipid component. The amphipathic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phos phatidylglycerols, phosphatidylserines, phosphatidylinositols, phosphatidic acids, etc. Examples of cationic amphipathic lipids are diacyl trimethylammoniumpropane and ethyl phosphatidylcholine. Examples of neutral lipids include diglycerides, such as diolein, dipalmitolein, and mixed caprylin caprin diglycerides; triglycerides, such as triolein, tripalmitolein, trilinolein, tricaprylin, and trilaurin; vegetable oils, such as soybean oil; squalene; tocopherol; and combinations thereof. Additionally, cholesterol or plant sterols can be used in making multivesicular liposomes.

As used herein, the term "biologically active," when used to describe IGF-I or any other agent present in the chambers of the multivesicular liposome, includes agents which possess biological activity targeted in treatment of a particular disease state, either in the form released from the MVL vesicles, or in a form that becomes active after release from the vesicle chamber, such as a pro-drug that is converted upon interaction with an enzyme into an active moiety with therapeutic activity.

The term "osmotic excipient" means any biologically compatible solute molecule, in an aqueous solution, that is not the biologically active agent. Both electrolytes and non-electrolytes function as osmotic excipients. In determining whether any particular molecule will function as an osmotic excipient or in determining the concentration of osmotic excipient encapsulated within a multivesicular liposome, consideration must be given to whether, under conditions within the multivesicular liposome (for example, pH), the molecule is wholly or partially ionized and whether such ions will permeate the lipid membrane (*The Bimolecular Lipid Bilayer Membrane,* Mahendra K. Jain, van Nostrand Reinhold Co., 1972, 470 pp.). One skilled in the art will appreciate that for use in the present invention, the osmotic excipient must be selected so as to avoid agents that would prove toxic or otherwise harmful to a subject undergoing therapy by use of the MVL of this invention. Those of skill in the art can readily evaluate the suitability of a given osmotic excipient for use in the present invention without resort to undue experimentation.

Certain osmotic excipients have inherent biological activity, and many facilitate the biological activity of the biologically active agent. For instance, calcium ions may be coencapsulated as a counterion to increase shelf life or facilitate bioactivity of a drug, but are not sufficient to accomplishing the therapeutic or other utility of the MVL formulation. In addition, various stabilizers may also be present. Certain agents commonly classified as excipients may actually possess direct biological activity from very slight to quite significant. For example, the common excipient mannitol can also act biologically as a diuretic, Even water may act biologically to cure dehydration, but when these compounds are used as osmotic excipients, they are relatively interchangeable with others that perform the same helper function.

Useful osmotic excipients include, but are not limited to, glucose, sucrose, trehalose, succinate, cyclodextrin, arginine, galactose, mannose, maltose, mannitol, glycine, lysine, citrate, sorbitol, dextran, and suitable combinations thereof, may be used to form multivesicular liposomes and to modulate the drug loading of the encapsulated agent from multivesicular liposomes. Table 1 below compares the osmolarity of sucrose and glycylglycine solutions at different concentrations.

TABLE 1

| Sucrose or Glycylglycine (w/v %) | Osmolarity for sucrose (mOsm) | Osmolarity for Glycylglycine (mOsm) |
| --- | --- | --- |
| 0.5 | 15 | 38 |
| 1.0 | 30 | 76 |
| 1.5 | 45 | 114 |
| 2.0 | 60 | 152 |
| 2.5 | 76 | 189 |
| 3.0 | 91 | 227 |
| 4.0 | 123 | 303 |
| 5.0 | 156 | 379 |
| 6.0 | 190 | 455 |
| 7.0 | 225 | 530 |
| 8.0 | 261 | 606 |

Useful pH modifying agents include, but are not limited to the organic acids such as citric, tartaric, maleic, gluconic, glucuronic, and succinic acids, and phosphoric acid.

As used herein the term "therapeutically effective amount or level" means the amount of a biologically active agent necessary to induce a desired pharmacological effect. The amount can vary greatly according to the effectiveness of a particular active agent, the age, weight, and response of the individual host as well as the nature and severity of the host's symptoms. Accordingly, there is no upper or lower critical limitation upon the amount of the active agent. The therapeutically effective amount to be employed in the present invention can readily be determined by those skilled in the art.

As used herein, "drug loading" means, in a general quantitative sense, the amount of the biologically active agent loaded into the product MVL suspension as compared with similar formulations. It is a measure, therefore, of the amount of active agent available in a unit volume of MVL formulation to be delivered to the patient during use. More particularly, "drug loading" means the ratio of drug per unit volume of liposome suspension to the percent encapsulated volume in the liposomes themselves. It is approximately equal to the concentration of the active agent in the MVL suspension divided by the lipocrit of the suspension, for low percent free drug.

$$\text{Drug Loading} = (\text{Drug Encapsulated Per Unit Volume of Liposome Suspension}) / (\text{Percent encapsulated volume in Liposomes})$$

$$\approx (\text{Drug Concentration of Liposome Suspension}) / \text{Lipocrit}$$

As used herein, "percent encapsulation of drug, or other compound" means the ratio of the amount of compound to be encapsulated in the final suspension of the liposome manufacturing process to the total amount of compound to be encapsulated used in the first aqueous solution of the process multiplied by 100.

$$\text{Percent encapsulation of compound} = \left( \left[ \frac{\text{Amt. of compound encapsulated}}{\text{Amt. of compound introduced prior to encapsulation}} \right] \right) \times 100$$

As used herein, "lipocrit," which is defined in analogy to hematocrit, means the ratio of the volume occupied by the liposomes to the total suspension volume multiplied by 100.

$$\text{Lipocrit (in percent)} = \left( \frac{[\text{Volume occupied by the liposomes}]}{[\text{Total volume of liposome suspension}]} \right) \times 100$$

As used herein, "percent free drug" means the ratio of the amount of drug exterior to the liposomes in the final liposome suspension to the total amount of drug in the final suspension (the final product) multiplied by 100.

$$\text{Percent free drug} = \left( \left[ \frac{\text{Amt. of drug exterior to the liposomes in the final product}}{\text{Amt. of drug in final product}} \right] \right) \times 100$$

$$\approx (1 - \text{Lipocrit}) \times \left( \frac{\text{Drug concentration exterior to the liposomes}}{\text{Drug concentration of liposome suspension}} \right)$$

The methods for determining these parameters are illustrated in Example 7 of this application.

In general, the lower limit for osmolarity of the first aqueous component can be close to zero, as in the case where the biologically active agent is encapsulated without any osmotic excipients. This is especially true if the active agent is a high molecular weight protein or other macromolecule. On the other hand, the osmolarity of the first aqueous component can be as high as about 1000 mOsm, or higher, without toxic effect because many of the excipients can pass out of the liposome during the process of manufacturing. Generally, however, the osmolarity of the first aqueous component is in the range from about 5 mOsm to about 320 mOsm.

The osmolarity of the encapsulated aqueous component in the final liposomal product is generally isotonic to that of the suspending medium, the physiologically relevant aqueous environment in which the MVLs are stored (such as 0.9 wt % saline), or into which they are introduced (both in vitro and in vivo). However, the osmolarity of the aqueous component in the final MVL product can also be hypertonic with respect to the physiologically relevant aqueous environment to provide an optimum decrease in the rate of release of the biologically active agent from the liposomes. Therefore, it is contemplated within the scope of this invention that the aqueous component in the MVL product can be hypotonic, isotonic or hypertonic with respect to the storage medium or the aqueous environment into which the biologically active agent is to be released.

Since the osmolarity of normal saline is similar to that of human plasma and other in vivo environments, such as cerebrospinal fluid, synovial fluid, and subcutaneous and intramuscular spaces, saline can be used as a predictive model of MVL drug release in such environments. Because the preferred use of the MVLs of the invention is for in vivo injection or implantation into tissue or body cavities (for instance, as drug depots), they are usually stored in a medium such as normal saline, phosphate-buffered saline, or other osmotically similar medium.

To assure sustained release in use and encapsulation efficiency during manufacture, the lipid component can comprise one or more amphipathic lipids having from about 13 to about 28 carbons, for example from about 18 to 22 carbons. This general rule holds whether the carbon chain of the amphipathic lipid is saturated, or whether it contains one or more double bonds. Generally, however, in selecting the lipids to be used in formulating a multivesicular liposome it should be kept in mind that it is possible to use an organic solvent with a lower boiling point when utilizing a lipid with a given number of carbons in the carbon chain, if the lipid contains at least one double bond in the carbon chain. . The beneficial effects upon encapsulation efficiency and sustained release of the biologically active agent to be obtained by utilizing such long chain amphipathic lipids during manufacture of MVLs is disclosed in copending U.S. patent application Ser. No. 08/723,583, filed Oct. 1, 1996, entitled "Method for Producing Liposomes With Increased Percent of Compound Encapsulated," which is incorporated herein in its entirety.

A representative list of long chain amphipathic lipids useful in the practice of this invention follows. This list is illustrative and not intended to in any way limit the scope of the invention. Also included are the abbreviations used to refer to the phospholipids in this application and in the scientific literature.

DEPC or DC22:1PC=1,2-dierucoyl-sn-glycero-3-phosphocholine
DOPC or DC18:1PC=1,2-dioleoyl-sn-glycero-3-phosphocholine
DLPC or DC12:0PC=1,2-dilauroyl-sn-glycero-3-phosphocholine
DMPC or DC14:0PC=1,2-dimyristoyl-sn-glycero-3-phosphocholine
DPPC or DC16:0PC=1,2-dipalmitoyl-sn-glycero-3-phosphocholine DSPC or DC18:0PC=1,2-distearoyl-sn-glycero-3-phosphocholine DAPC or DC20:0PC=1,2-diarachidoyl-sn-glycero-3-phosphocholine DBPC or DC22:0PC=1,2-dibehenoyl-sn-glycero-3-phosphocholine DC16:1PC=1,2- dipalmitoleoyl-sn-glycero-3-phosphocholine DC20:1PC=1,2-dieicosenoyl-sn-glycero-3-phosphocholine DC22:1PC=1,2-dierucoyl-sn-glycero-3-phphohocholine DPPG=1,2-dipalmitoyl-sn-glycero-3-phosphoglycerol DOPG=1,2-dioleoyl-sn-glycero-3-phosphoglycerol The preferred amphipathic lipids for use in making the multivesicular liposomes of this invention are DOPC and DEPC, naturally occurring lipids.

High loading formulations of IGF-I obtained by the method of this invention are particularly useful in the pharmaceutical industry for reducing the amount of liposome formulation that must be administered to a subject (e.g., intramuscularly or subcutaneously) to achieve a desired therapeutic concentration of drug in the blood stream. They are also useful for reducing the number of times the IGF-I must be administered to attain a sustained therapeutic level of drug in the patient. The upper useful limit on the amount of drug encapsulated into a given volume of liposome suspension may also be dictated by the lipocrit of the suspension. As one skilled in the art will appreciate, it may be difficult to inject a suspension containing liposomes if the lipocrit of the suspension is too high. For systemic administration, the dosage range of IGF-I in multivesicular liposomes appropriate for in vivo use in humans of this invention includes the range of about 0.01 mg/kg up to about 100 mg/kg of lean body mass, or higher, depending on the therapeutic indication. For example, in treatment of diabetes or ALS, one would select the upper end of the dosage range. However, for local injection or delivery, the lower end of the systemic dosage range would be selected.

Both the high load and low load formulations can be further diluted to obtain an injectable slow release depot formulation of any therapeutically effective total dosage by addition of suspending medium or any physiologically acceptable carrier. Common suitable carriers include aqueous or non-aqueous solutions, suspensions, and emulsions. Examples of non-aqueous solutions are propylene glycol, polyethylene glycol, vegetable oils, such as olive oil, and injectable organic esters such as ethyl oleate. Aqueous carriers include water, alcoholic-aqueous solutions, emulsions or suspensions, including saline and buffered media. Parenteral vehicles include sodium chloride solution, Ringer's dextrose, dextrose, and lactated Ringer's solution. Intravenous vehicles include fluid and nutrient replenishers, electrolyte replenishers (such as those based on Ringer's dextrose), and the like. Preservatives and other additives may also be present, such as, antimicrobials, anti oxidants, chelating agents, and inert gases (see, *Remingtons Pharmaceutical Sciences,* 16th Ed., A. Oslo, ed., Mack, Easton, Pa. 1980).

The compositions of IGF-I in MVL retain substantially full bioactivity and may be administered by any desired route; for example, intratumoral, intra-articular (into joints), intra-ocular, intramuscular, intrathecal, intraperitoneal, subcutaneous, intravenous, intralymphatic, oral and submucosal. The multivesicular liposomes may be modified using methods well known in the art by attaching thereto, either directly, or indirectly, such as by means of a excipient molecule or peptide, target-specific ligands, such as antibodies and other receptor specific protein ligands, in order to impart organ or cell target specificity (Malone, et al., *Proc. Nat'l. Acad. Sci, U.S.A.,* 86:6077, 1989; Gregoriadis, *Immunology Today,* 11(3):89, 1990; both incorporated by reference).

A series of experiments were conducted to show that the effect of osmolarity upon drug loading is inverse and is independent of other parameters used during the manufacturing process, including the type of mixer used during formation of emulsions. High load formulations were obtained using first aqueous components containing concentrations of IGF-I ranging from 20 to 80 mg/mL of IGF-I and either with or without 25 mM citric acid. In addition, IGF-I formulations were made comparing the effects upon drug loading using a sugar (sucrose) or a non-sugar (glycylglycine) as the osmotic excipient. Comparison of the results of these tests in Tables 2 through 6 showed that the inverse relationship between osmolarity and drug loading is not dependent upon the chemical character of any of the components that make up the first aqueous component, and that it depends only upon one parameter, the overall osmolarity of the first aqueous component used during manufacture of the MVLs. In a number of the formulations, the long-chain amphipathic lipid used to impart slow release properties of the formulations was switched from DEPC to DOPC without significant change of the trend of modulation of drug loading by altering osmolarity. In addition, the MVL formulations were made in different batch sizes with different types of mixers to illustrate that the method of this invention is independent of such variables used during the process.

The following examples illustrate the manner in which the invention can be practiced. It is understood, however, that the examples are for the purpose of illustration, and the invention is not to be regarded as limited to any of the specific materials or conditions therein.

EXAMPLE 1

Preparation of High Load IGF-I-containing Multivesicular Liposome Formulations

A. A 0.5 mL scale preparation of MVLs.

In all of the methods of making MVLs illustrated herein, in the first step, a 'water-in-oil' emulsion was prepared by mixing a lipid component with a first aqueous component. The lipid component contained 0.5–4 mL of 13.20 mM DOPC or DEPC, 19.88 mM cholesterol, 2.79 mM DPPG, and 2.44 mM triolein (Avant Polar Lipids Inc., Alabaster, Ala.) in chloroform (Spectrum Chemical Manufacturing Corp., Gardena, Calif.) as solvent.

In the present embodiment, a lipid component containing DEPC rather than DOPC was prepared. The first aqueous component contained 50 mg/mL of IGF-I and 0.25 0.5, 1.0 2.5 r 5.0 w/v % of sucrose as osmotic excipient. An emulsion of the lipid and first aqueous components was formed by mixing 0.5 mL of the first aqueous component with 0.5 mL of the first aqueous component with 0.5 mL of the lipid component using a Baxter vortexer at maximum speed (setting 10) for 6 min. To the resulting first emulsion, 2.5 mL of a solution containing 4 wt % glucose and 40 mM lysine (Spectrum Chemicals) was added, respectively. The resulting mixture was emulsified to form a second emulsion with the Baxter vortexer at maxium speed for 4 sec. The resulting second emulsion, a "water-in-oil-in-water" double emulsion, was transferred for gentle swirling to a 250 mL erlenmeyer flask containing 10 mL of a solution of 4 percent by weight glucose and 40 mM lysine. To evaporate the organic solvent (chloroform) from the particles, nitrogen gas was passed over the second emusion at 37° C. for 20 minutes with gentle shaking. The resulting multivesicular liposomes were washed twice with 50 mL of normal saline by centrifugation at 600×g on a bench top centrifuge, and then resuspended in 0.5–4 mL of normal saline. The estimated osmolarity (mOsm), percent yield and drug. The remainder of the steps described in Example 1 were carried out to obtain MVLs containing IGF-I suspended in normal saline. The estimated osmolarity (mOsm), percent yield, and drug loading of these formulations are shown in Table 2 below:

TABLE 2

| First Aqueous Component | | | | Final | |
|---|---|---|---|---|---|
| | | | Estimated | Liposome Suspension | |
| IGF-I (mg/mL) | Sucrose (w/v %) | Other | Osmolarity (mOsm) | % Yield | Drug Loading (mg/mL) |
| 20 | 5.0 | 100 mMHCl | 347.0 | 51.6 | 37.7 |
| 20 | 2.5 | 100 mMRCl | 267.0 | 47.5 | 46.1 |
| 50 | 2.5 | 100 mMHCl | 271.0 | 44.6 | 45.7 |
| 50 | 0.0 | 100 mMHCl | 195.0 | 53.4 | 73.2 |

When the encapsulated IGF-I was characterized as described in Example 3 herein, it was discovered that the protein was somewhat denatured. Further study shows that use of citric acid provides a more favorable chemical conditions for bioactivity of encapsulated IGF-I.

B. A 4 mL scale preparation of MVLs

A lipid component containing DOPC rather than DEPC was prepared as in Example 1. The first aqueous component contained 20 mg/mL of IGF-I (Chiron Corp., Emeryville, Calif.) in 100 mM hydrochloric acid, and 2.5 or 5.0 w/v % of sucrose as osmotic excipient, or 50 mg/mL of IGF-I in 100 mM hydrochloric acid and 0 or 2.5 w/v % of sucrose as osmotic excipient. The procedures of Example 1 were followed for obtaining the MVLs containing IGF-I, except that 4 mL of the first aqueous component was mixed with 4 mL of the lipid component using a TK Autohomogeneizer K at a speed of 9,000 rpm for 8 min to obtain the first emulsion. To the first emulsion, 1 mL of a solution containing 4 wt % glucose and 40 mM lysine (Spectrum Chemicals) was added, respectively. The resulting mixture was emulsified to form a second emulsion with the TK Autohomogeneizer K at a speed of 4,000 rpm for 1 min. The estimated osmolarity (mOsm), percent yield, and drug loading of these formulations using a vortexer mixer and DEPC, a lipid having a 22 carbon chain, are shown in Table 3 below:

TABLE 3

| First Aqueous Component | | | | Final | |
|---|---|---|---|---|---|
| | | | Estimated | Liposome Suspension | |
| IGF-I (mg/mL) | Sucrose (w/v %) | Other | Osmolarity (mOsm) | % Yield | Drug Loading (mg/mL) |
| 50 | 5.0 | 0.0 | 162.7 | 57.0 | 49.8 |
| 50 | 2.5 | 0.0 | 82.7 | 62.4 | 76.8 |
| 50 | 1.0 | 0.0 | 36.7 | 54.9 | 97.4 |
| 50 | 0.5 | 0.0 | 21.7 | 66.0 | 157.1 |
| 50 | 0.25 | 0.0 | 14.2 | 67.0 | 159.4 |

Table 3 shows that the results obtained with the TK mixer procedure are similar to those obtained when a vortexer mixer is used to make the emulsions. When the encapsulated protein was obtained and characterized as described in Example 3 herein, an increased amount of IGF-I oligomers was found as compared with the formulations of Table 4 wherein 25 mM citric acid was included in the first aqueous component.

C. A 3 mL scale preparation of encapsulated IGF-I.

A lipid component containing DEPC rather than DOPC was prepared as in Example 1. The first aqueous component contained 30 mg/mL of IGF-I in 25 mM citric acid, and 0 or 2.5 w/v % of sucrose as osmotic excipient, or 50 mg/mL of IGF-I in 25 mM citric acid, and 2.5, 1.0, 0.5 or 0 w/v % of sucrose, or 50 mg/mL of IGF-I without citric acid, and 0 or 0.5 w/v % of sucrose. The procedures of Example 1 were followed for obtaining the MVLs containing IGF-I, except that 3 mL of the first aqueous component was mixed with 3 mL of the lipid component using an Omni Mixer ES at a speed of 10,000 rpm for 12 min to obtain the first emulsion. To the first emulsion, 20 mL of a solution containing 4 wt % glucose and 40 mM lysine (Spectrum Chemicals) was added, respectively. The resulting mixture was emulsified to form a second emulsion with the Omni Mixer ES at a speed of 4,500 rpm for 2 min. The estimated osmolarity (mOsm), percent yield, and drug loading of these formulations are shown in Table 4 below:

TABLE 4

| First Aqueous Component | | | | Final | |
|---|---|---|---|---|---|
| | | | Estimated | Liposome Suspension | |
| IGF-I (mg/mL) | Sucrose (w/v %) | Other | Osmolarity (mOsm) | % Yield | Drug Loading (mg/mL) |
| 30 | 2.5 | 25 mM Citric Acid | 106.8 | 69.2 | 54.8 |
| 30 | 0.0 | 25 mM Citric Acid | 30.8 | 57.2 | 132.2 |
| 50 | 0.5 | 0.0 | 21.7 | 80.0 | 171.4 |
| 50 | 0.0 | 0.0 | 6.7 | 72.7 | 267.5 |
| 50 | 2.5 | 25 mM Citric Acid | 109.5 | 60.3 | 82.5 |
| 50 | 1.0 | 25 mM Citric Acid | 63.5 | 72.3 | 138.2 |
| 50 | 0.5 | 25 mM Citric Acid | 48.5 | 7.5 | 174.2 |
| 50 | 0.0 | 25 mM Citric Acid | 33.5 | 65.8 | 175.7 |

The results in Table 4 show a similar modulation of drug loading by osmolarity for any of the drug concentrations tested.

EXAMPLE 2

Effect of Substituting Glycylglycine as the Osmotic Excipient

A lipid component containing DEPC rather than DOPC was prepared as in Example 1. The first aqueous component contained 10 mg/mL of IGF-I in 25 mM citric acid, and 0, 1.0 or 2.0 w/v % of glycylglycine as osmotic excipient. The remainder of the steps described in Example 1 were carried out to obtain MVLs containing IGF-I suspended in normal saline. The estimated osmolarity (mOsm), percent yield, and drug loading of these formulations are shown in Table 5 below.

TABLE 5

| First Aqueous Component | | | | Final | |
|---|---|---|---|---|---|
| | | | Estimated | Liposome Suspension | |
| IGF-I (mg/mL) | Sucrose (w/v %) | Other | Osmolarity (mOsm) | % Yield | Drug Loading (mg/mL) |
| 10 | 5.0 | 25 mM Citric Acid | 180.1 | 64.0 | 10.4 |

TABLE 5-continued

| First Aqueous Component | | | Estimated Osmolarity (mOsm) | Final Liposome Suspension | |
|---|---|---|---|---|---|
| IGF-I (mg/mL) | Sucrose (w/v %) | Other | | % Yield | Drug Loading (mg/mL) |
| 10 | 1.0 | 25 mM Citric Acid | 104.1 | 53.0 | 13.0 |
| 10 | 0.0 | 25 mM Citric Acid | 28.1 | 41.7 | 24.4 |

A similar osmotic modulation of drug loading is shown for formulations using a non-sugar osmotic spacer, glycylglycine, in place of sucrose. Thus, the effect of osmolarity upon drug loading is shown by the data in Table 5 to be independent of the chemical structure of the osmotic excipient used.

Comparison of different Osmotic Excipients at Equal Osmotic Strength

MVLs were made in the method of Example 1A containing IGF-I encapsulated with either 2.5 w/v % sucrose or 1.0 w/v % glycylglycine as osmotic excipients at approximately equal osmotic strength. For the comparison, 2.5 w/v % sucrose or 1.0 w/v % glycylglycine as the osmotic excipient was introduced into the first aqueous component containing 80 mg/mL IGF-I and 25 mM citric acid.

The procedures of Example 1A were followed for obtaining the MVLs containing IGF-I, except that 3 mL of the first aqueous component was mixed with 3 mL of the lipid component using an Omni Mixer ES at a speed of 10,000 rpm for 12 min to obtain the first emulsion. To the first emulsion, 20 mL of a solution containing 4 wt % glucose and 40 mM lysine (Spectrum Chemicals) was added, respectively The resulting mixture was emulsified to form a second emulsion with the Omni Mixer ES at a speed of 4,500 rpm for 2 min.

To determine whether the effect upon drug loading is attributable solely to the osmolarity of the first aqueous component, a third formulation was made as described above, except that the concentrations of the osmotic excipient and the IGF-I were both proportionately decreased (from 80 mg/mL IGF-I and 2.5% sucrose to 50 mg/mL IGF-I and 1.0% sucrose. In these formulations, the second aqueous component substituted 1.5% glycine and 40 mM lysine in place of the 4% glucose and 40 mM lysine used in Example 1. Table 6 below compares the estimated osmolarity, % Yield and Drug Loading in the final liposome suspension for these three formulations.

A comparison of the estimated osmolarity (mOsm), percent yield, and drug loading of these formulations are shown in Table 6 below:

TABLE 6

| First Aqueous Component | | | Estimated Osmolarity (mOsm) | Final Liposome Suspension | |
|---|---|---|---|---|---|
| IGF-I (mg/mL) | Osmtoic spacer (w/v %) | Other | | % Yield | Drug Loading (mg/mL) |
| 80 (A) | 2.5% Sucrose | 25 mM Citric Acid | 113.5 | 85.9 | 145.1 |

TABLE 6-continued

| First Aqueous Component | | | Estimated Osmolarity (mOsm) | Final Liposome Suspension | |
|---|---|---|---|---|---|
| IGF-I (mg/mL) | Osmtoic spacer (w/v %) | Other | | % Yield | Drug Loading (mg/mL) |
| 80 (B) | 1% Glycyl-glycine | 25 mM Citric Acid | 113.5 | 77.4 | 156.4 |
| 50 (C) | 1% Sucrose | 25 mM Citric Acid | 63.5 | 75.7 | 142.5 |

The data in Table 6 show that for a given drug concentration, the osmolarity of the osmotic excipient is the result effective variable because two different osmotic spacers at approximately equal osmotic strength but at unequal weight concentration produce a comparable effect upon drug loading. On the other hand, the drug concentration in the first aqueous component can also affect drug loading.

The data in Tables 2–6 show that drug loading in a high load MVL-IGF-I formulation can be modulated by varying the osmolarity of the first aqueous solution used in making multivesicular liposomes, with decreasing of osmolarity resulting in increased drug loading.

EXAMPLE 3

Determination of Percent Encapsulation (or Percent Yield), Lipocrit, Percent Free Drug, Particle Size Distribution, and Drug Loading in High Load Formulations of IGF-I Tables 2 through 4 show the estimated osmolarity (mOsm), % Yield and Drug Loading (mg/mL) for the high load liposomal formulations described in Examples 1 and 2 above. Percent encapsulation (or percent yield) of drug was calculated as the percent ratio of the amount of drug in the final liposome suspension to the total amount of drug used in the first aqueous solution. Thus, percent yield of drug was calculated as the ratio of the drug concentration in the final suspension times the volume of the final suspension to the drug concentration in the first aqueous solution times the volume of the first aqueous solution. Lipocrit was calculated, in analogy to hematocrit, as the percent ratio of the pellet volume to the suspension volume (see conditions below for obtaining the pellet volume).

Percent free drug was calculated as the percent ratio of the amount of drug in the supernatant to the amount of drug in the final suspension. Percent free drug can also be calculated as the percent ratio of the drug concentration in the supernatant to that in the suspension, times (1-lipocrit) Drug loading, which measures the amount of drug encapsulated in each unit of the encapsulated volume, is approximately equal to and can be estimated (assuming low percent free drug) as the ratio of the drug concentration of the final liposome suspension to the lipocrit. These variables were determined as more particularly described below.

To calculate the lipocrit, about 50 μL of the multivesicular liposome suspension was taken up into a capillary tube, and end of the tube was sealed while ensuring that the suspension contained no air bubbles. The suspension was spun in a centrifuge at 600×g for 10 minutes to obtain a pellet layer and a supernatant layer. The lipocrit was calculated as the percent ratio of the length of the tube occupied by the pellet to that occupied by the suspension.

For use in determining the amount of free drug in a formulation, supernatant was obtained by centrifuging about 0.2 mL of suspension for 3 min at 600×g in an Eppendorf centrifuge tube. The absorbance at 280 nm was then measured on a spectrophotometer (Hitachi U-2000). For centrifugation, 25–50 μL of the supernatant was withdrawn and pipetted into a glass tube containing 1 mL of 3:1 v/v isopropyl alcohol:2N citric acid (Sigma Chemical), followed by rigorous mixing to obtain a clear solution. The absorbance at 275 nm was measured on a spectrophotometer (Hitachi U-2000). Using a reference absorbance standard established based on drug solutions of known concentration in the same dissolving solution, the concentrations of drug in the suspension and supernatant were calculated. The range of free drug in the high load formulations was generally <2% (w/v).

Particle size distribution and particle mean diameter were determined by the method of laser light diffraction using a LA-500 or LA-910 Particle Size Analyzer from Horiba Inc. (Irvine, Calif.). The volume-weighted mean particle diameter for all the formulations studied was generally in the range from about 6 to 18 μm.

EXAMPLE 4

In Vitro and In Vivo Release of High Drug Loading, High Percent Yield IGF-I Formulations The physicochemical integrity of the encapsulated high load IGF-I was confirmed by SDS-PAGE assay using Novex NuPage gel as well as by RP-HPLC assay using a C18 symmetric column. The encapsulated protein was extracted using 75:25 IPA:2N Citric Acid. The bioactivity of the encapsulated IGF-I was confirmed by a mitogenic bioassay using MG-63 cells and MTT stain according to the method of W. Lopaczynski et al., *Regulatory Peptides*, 48:207–216, 1993. The MG-63 human osteosarcoma cell line was obtained from the American Type Culture Collection (ATCC# CRL 1427) and the dose dependent mitogenic response of quiescent MG-63 cells to added IGF-I was determined. Bioactivity of extracted IGF-I was confirmed as approximately equivalent to that of an unencapsulated standard.

Figure 2:
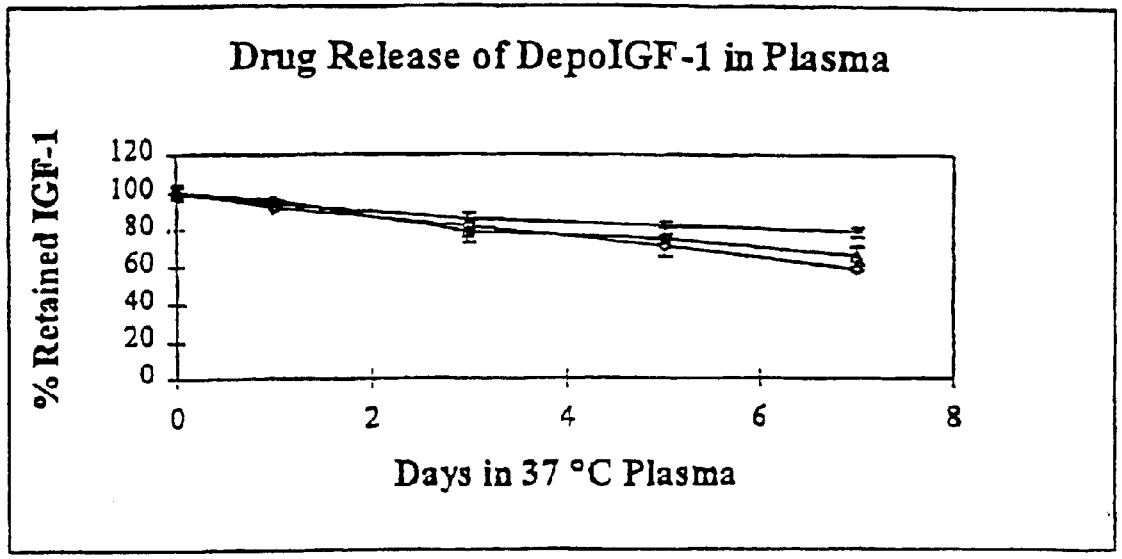
FIG. 2 is a graph showing the plasma release characteristics of IGF-I encapsulated in multivesicular liposomes corresponding to the formulations in Table 6.

In vitro Experiment: Briefly, an in vitro release experiment was set up and conducted as follows: a MVL suspension containing about 50 mg/mL of IGF-I was diluted 20-fold into human plasma containing 0.01% $NaN_3$; a 0.5 mL sample in screw-cap Eppendorf tube was used for each time-point, and samples were incubated under dynamic/rotating conditions at 37° C. Time-point samples were taken at various times and washed with 0.9 mL of normal saline. Particle pellets were then obtained by centrifugation in a microfuge at 14 K rpm about 16,000 g for 4 minutes and stored at −20° C. until assayed by RP-HPLC using a C18 symmetric column. FIG. 2 shows in vitro plasma release data obtained for the three representative IGF-I formulations listed in Table 5. These data indicate that a sustained release of IGF-I is achieved in all three formulations tested over a period of longer than a week for high drug loading, high yield IGF-I formulations.

In vivo Experiment: Male rats were injected subcutaneously with the three MVL formulations shown in Table 6 to obtain information about in vivo release characteristics. Each rat received a 10 mg dose of IGF-I, and each of the formulations tested was injected into 3 rats. Blood samples (0.2 mL) were collected from the tail vein of the rats and allowed to clot at time zero, and at 1, 3, 5 and 7 days post injection. Serum was then obtained by centrifugation, and stored at −70° C. prior to assay for IGF-I concentration using an IGF-I ELISA kit DSL-10-5600 (Diagnostic Systems Laboratories Inc., Webster, Tex.).

Figure 3:
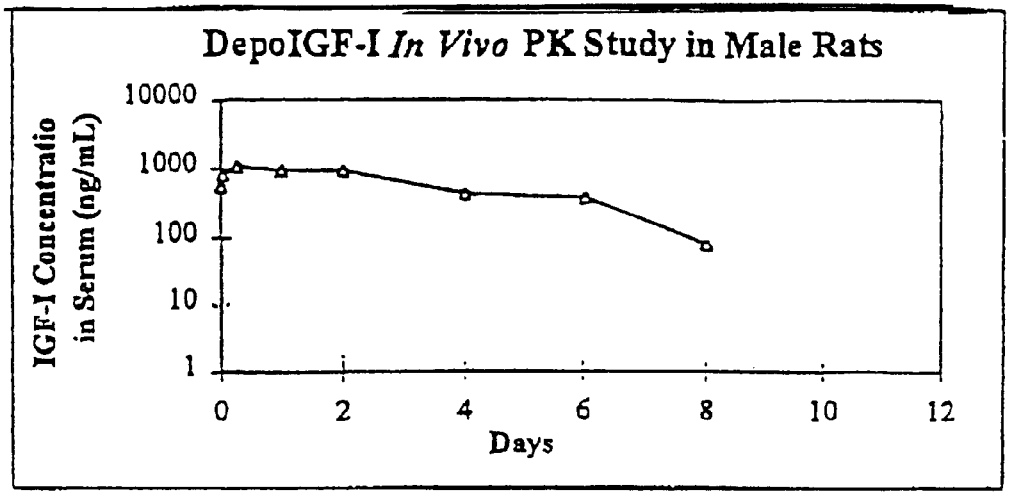
FIG. 3 is a graph showing the IGF-I concentration in serum (mg/mL) over 8 days in male rats after a 10 mg subcutaneous injection of MVLs made with 80 mg/mL IGF-I, 25 mM citric acid, and 2.5 w/v % sucrose (113.5 mOsm) in the first aqueous component. The data represent the mean of three rats.

FIG. 3 shows the time course of the average serum IGF-I concentration of three rats that received the 10 mg IGF-I of Formulation A in Table 6. These data indicate that a sustained serum level of IGF-I can be achieved over a period of many days using the high drug loading, high yield IGF-I formulations of this invention.

EXAMPLE 5

Preparation of Low Load IGF-I-Containing MVLs

MVL containing a low loading of IGF-I were prepared by modification of the method of Example 1A as follows: the aqueous component was an aqueous solution containing a concentration of IGF-I in the range from 9–16 mg/mL in 7% sucrose (w/v) 20 mM ammonium citrate (pH 5). An aliquot of 3.5 mL of the aqueous component was emulsified at ambient temperature (23–28° C.) for 9 minutes at 9,000 rpm with an equal volume of a lipid component containing 13 mM dioleoyl phosphatidylcholine, 2.8 mM dipalmitoyl phosphatidylglycerol, 19.9 mM cholesterol, and 2.4 mM tripalmitolein dissolved in water saturated cholesterol. After mixing, 28 mL of 4% glucose in 20 mM lysine was added to the water-in-oil emulsion with the mixing blade at 1 cm above the organic aqueous interface, and the contents mixed for 1 minute at 6,000 rpm. The resulting second emulsion as added to a 1 L baffled flask containing 42 mL of 4% glucose in 20 mM lysine. The mixture in the flask was sparged with 50 standard cubic feet per hour Nitrogen at 37° C. for 15 minutes to remove the chloroform. The multivesicular liposomes were then harvested by adding 4 times the post-sparge volume of 122 mM Ammonium Citrate Dibasic (pH 5), and centrifuging for 10 minutes at 627 g. After washing, the pellet was resuspended in an equal volume of 122 mM Ammonium citrate Dibasic, at a lipocrit of about 40–50%. Encapsulation efficiency of IGF-I in the MVL was calculated at greater than 60%. The osmolarity range that corresponds to 9–16 mg/mL of IGF-I in 7% sucrose in 20 mM ammonium citrate dibasic is about 30 mOsm to about 290 mOsm.

EXAMPLE 6

Characterization of the Low Load IGF-I-Containing Formulations

Particle Size. The size of the MVL particles was determined by using a Horiba model LA-500 laser light scattering particle size detector (Horiba Instruments, Inc. Irvine, Calif.) Raw Data was collected using Horiba LA-500 software (Horiba Instruments, Inc. Irvine, Calif.) Particle sizing was done by adding 10–15 μl of MVL suspension to 10 mL of 0.9% NaCl and measuring the volume-weighted distribution of size. The median particle size ranged from 12–18 microns.

Lipocrit. Lipocrit was measured by adding 65 μL of MVL suspension to microhematocrit tubes and spinning the microhematocrit tubes (Fisher Scientific, Pittsburgh, Pa.) for 10 minutes at 630 g. After spinning, the supernatant and pellet lengths were measured. The lipocrit was calculated As the percent ratio of the length of the tube occupied by the pellet to that occupied by the suspension.

Microscopy. Liposome suspensions were observed pictorially under an Olympus (BH-2) microscope. The suspensions were diluted 3-fold with 0.9% Sodium chloride solution, prior to observation. The liposomes were essentially spherical and multivesicular.

pH of encapsulated aqueous component. The pH of the aqueous component encapsulated within the MVLs in the final formulation was estimated by washing the MVL pellet obtained by centrifugation with saline and then resuspending the pellet with HPLC grade water (Mallinckrodt-Baker, Paris, Ky). Then the sample was frozen at −70° C. to fracture the vesicles, thereby releasing the encapsulated aqueous component from the MVL. The pH of the released aqueous component was measured in HPLC water and corrected for dilution by the HPLC water to obtain the estimated pH of the encapsulated aqueous component.

EXAMPLE 7

A 125 ml Scale Preparation of Encapsulated IGF-I

A standard lipid component containing DEPC rather than DOPC was prepared as for other drug formulations. The first aqueous component contained 15 mg/mL IGF-I dissolved in either a 5% sucrose/20 mM ammonium citrate solution, or in a 8% sucrose/20 mM ammonium citrate solution. 125 mL of first aqueous solution was mixed with 125 mL of the lipid component using a high-shear double-mixing vessel system to obtain the first emulsion. This mixing system models the production scale process, and is used for scale-up of encapsulated drug formulations. The aqueous and organic components were mixed at a speed of 8000 rpm for 30 minutes in the first emulsion vessel. The first emulsion was then pumped at a rate of 167 mL/min into a fluid stream consisting of 0.04 N ammonium hydroxide in 1.5% glycine solution flowing at 2400 mL/min, and blended using an in-line static mixer to obtain the second emulsion. The total flow rate through the static mixer was 2567 mL/min. At this rate, the first emulsion was depleted in 90 seconds. The second emulsion, upon entry into a receiving vessel was mixed with lysine solution, and then was immediately sparged with nitrogen to strip off the organic solvent. The estimated osmolarity (mOsm), percent yield, drug loading, and % free-drug for these formulations are shown in Table 7 below.

procedure used was a modification of a procedure used for extraction of IGF-I from its plasma binding proteins, and was as follows: a 100 uL sample of a test suspension was centrifuged for 10 minutes at 627 g. Supernatants were aspirated from the particle fractions, and saved for analysis. Each particle fraction was then extracted using 87% Isopropanol 13% 2N hydrochloric acid solution. Extracted samples were incubated in an ice bath for 45 minutes, then neutralized with a 1 M concentration solution of Tris/Hydrochloric acid at pH 9.

Protein concentration was measured at 275 nm on a Hitachi model U-2000 spectrophotometer (Hitachi Scientific Instruments, Berkshire, UK). The protein concentration was calculated using the extinction coefficient of 0.62 for a protein solution containing 1 mg/ml IGF-I. The free IGF-I concentration was determined by the absorbance of a dilution of the stock IGF-I solution in 100 mM acetic acid.

The encapsulated IGF-I was also characterized by RP-HPLC after extraction, and compared to the free IGF-I. RP-HPLC was carried out on a Hewlett-Packard model 1090 liquid chromatography system (Hewlett-Packard GmbH, Waldborn, Germany). The column used was a 150×3.9 nm I.D. Waters Symmetry $C_{18}$ (Millipore, Milford, Mass.). Raw data was collected using Hewlett-Packard 3D Chemstation software (Hewlett-Packard GmbH, Waldborn, Germany). IGF-I was detected at both 214 nm and 275 nm.

IGF-I was separated at a flow rate of 0.8 ml/min, using a linear solvent gradient, starting with 22 volume percent of solvent B and changing to 40 volume percent B over 11 minutes. Solvent A was 10% acetonitrile/0.2% trifluoroacetic acid and buffer B was 90% acetonitrile/0.2% trifluoroacetic acid (TFA). Separation was followed by a 4 minute isocratic elution with 100% solvent B, followed by a 9-minute equilibration at initial conditions. Separation was conducted at 45 degrees C.

SDS-PAGE analyses of the IGF-I separated from MVL of the IGF-I were performed according to the manufacturer's instructions using Novex 18% Tris/glycine gels and the Novex Tris/Glycine buffer system. SDS PAGE gel analysis of MVL encapsulating IGF-I indicated an absence of oligomerization and showed that the integrity of the encapsulated protein was maintained.

TABLE 7

| First Aqueous Solution | | | Final Liposome Suspension | | | | |
|---|---|---|---|---|---|---|---|
| | | | | | | Drug | |
| IGF-I (mg/mL) | Sucrose (w/v %) | Other | Estimated Osmolarity | % Yield | Susp (mg/ml) | % Lipocrit | Loading (mg/ml) | % Free IGF-I |
| 15 | 8.0 | 20 mM ammonium citrate | ~321 mOsm | 42 | 5.1 | 41.8 | 12.2 | 0.18 |
| 15 | 5.0 | 20 mM ammonium citrate | ~216 mOsm | 56 | 5.8 | 36.7 | 15.8 | 0.24 |

The results in Table 7 above show a similar increase in drug loading by decreased sucrose concentration as for the other drug formulations tested.

EXAMPLE 8
Characterization of IGF-I in the Low Load MVL Formulations

Figure 4:
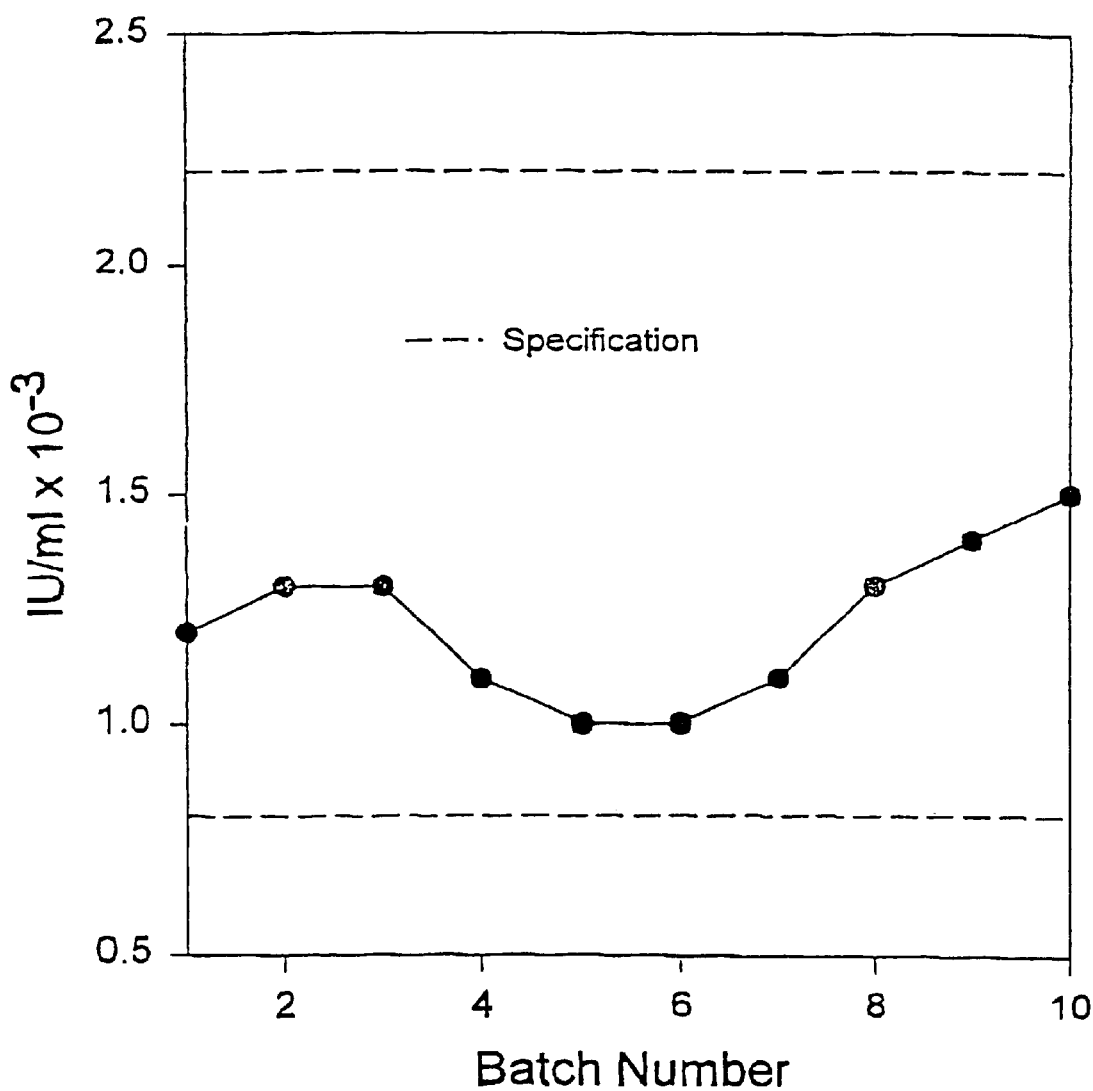
FIG. 4 is a graph showing the bioactivity in international units (IU) of IGF-I extracted from 10 batches of low load MVL formulations containing the IGF-I in a concentration of about 5 mg/mL of formulation made according to the method of the invention. The bioactivity is measured using a cell culture mitogenic assay with a standard rhIGF-I control having an activity of ~1.3×10$^3$ international units (IU)/mL.

The IGF-I was extracted from the particles prior to the characterization of the encapsulated protein. The extraction The bioactivity of the encapsulated IGF-I was confirmed by a mitogenic bioassay using MG-63 cells, a human osteosarcoma cell line, 3-(4,5-dimethylthiazol-2-yl)-2,5 diphenyltetrazolium bromide (MTT) stain according to the method of W. Lopaczynski et al., *Regulatory Peptides*, 48:207–216, 1993. The MG-63 cell line was obtained from the American Type Culture Collection (ATCC# CRL 1427), and the dose dependent mitogenic response of quiescent MG-63 cells to added IGF-I was determined. FIG. 4 shows the bioactivity of a low load MVL formulation of IGF-I containing 5 mg IGF-I per mL of formulation as calculated against a standard of recombinant human IGF-I (Chiron Corporation) with bioactivity of $1.3 \times 10^3$ international units (IU)/mL. Recoveries in the mitogenic assay ranged from 90–110% of the control IGF-I.

Figure 5:
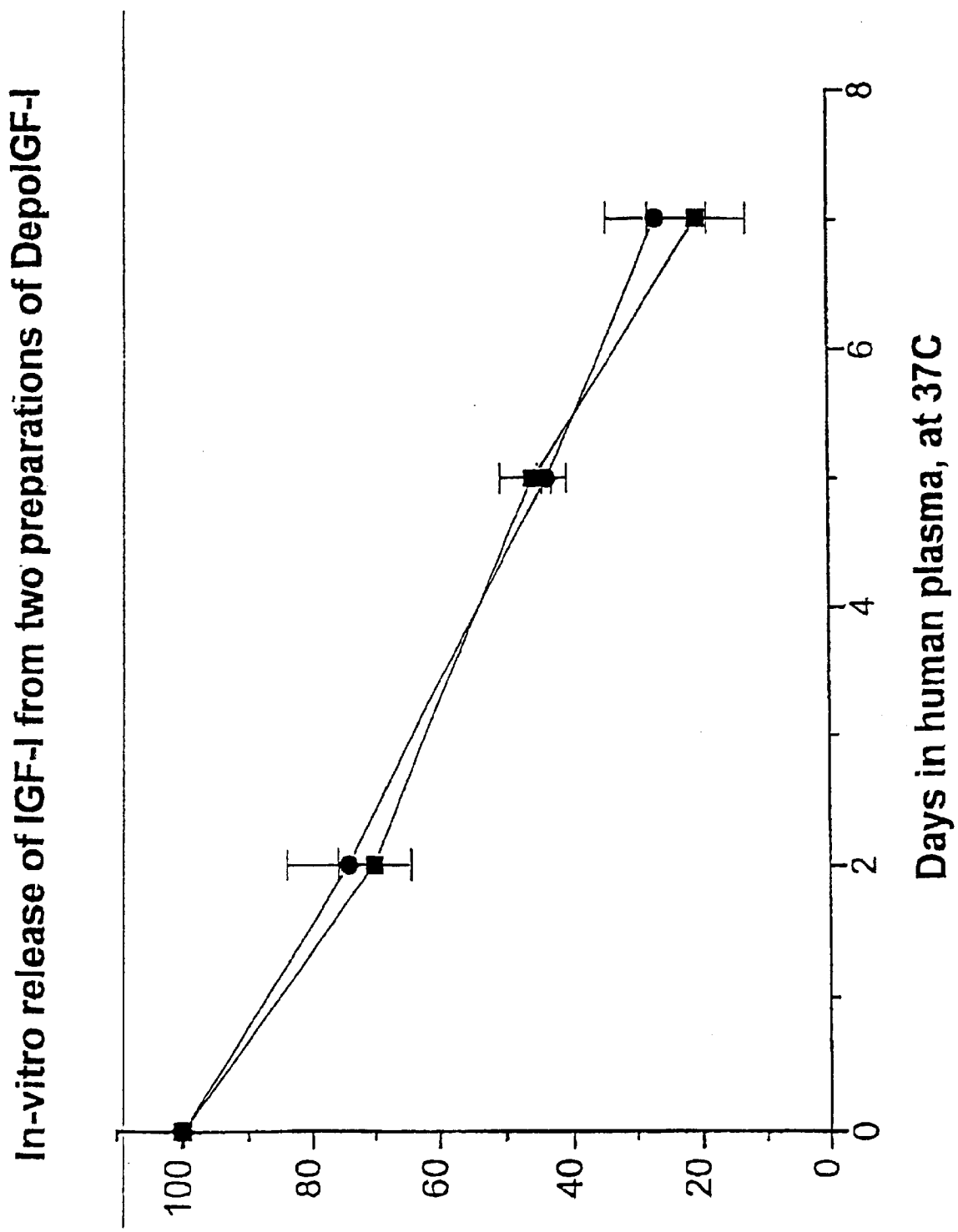
FIG. 5 is a graph showing the in vitro release profile in human plasma over 7 days of IGF-I encapsulated as a low load formulation (5 mg/mL) in MVL. The ordinate shows the percent of IGF-I retained in the particle fraction, and the abscissa shows the days of incubation in plasma at 37° C.

In-vitro studies. To estimate the rate of release in plasma of low load IGF-I from the low load multivesicular liposomes in vitro, blood bank human plasma (spiked with 0.01% sodium azide) was incubated with MVL suspensions containing a five-fold dilution of the 5 mg/mL MVLs, as compared with a 20-fold dilution of the high load formulation. 500 uL aliquots were pipetted into 1.5 mL screw cap tubes, with each tube representing one time point, and incubated at 37° C. under gently dynamic conditions. All in vitro release studies were set up in duplicate. At timepoints 1, 3, 5 and 7 days after the start of incubation, 0.9 mL of 0.9% sodium chloride was added to one of the tubes. The tube was spun for 3 minutes at 14,269 g in a microcentrifuge, and the supernatant and pellet was separated. The pellet was extracted with 1 mL acidified isopropanol and 0.2 ml Tris as described above under extraction procedure. The extracted pellets were analyzed for IGF-I content by RP-HPLC. For the determination of the bioactivity of IGF-I released from the MVL particles, the suspension was incubated in saline at 37° C., and the IGF-I bioactivity was measured in both the supernatant and pellet fractions as described above. A graph of the in vitro release profile (FIG. 5) shows that by 7 days 75–80% of encapsulated IGF-I is released in a sustained zero-order manner.

Figure 6:
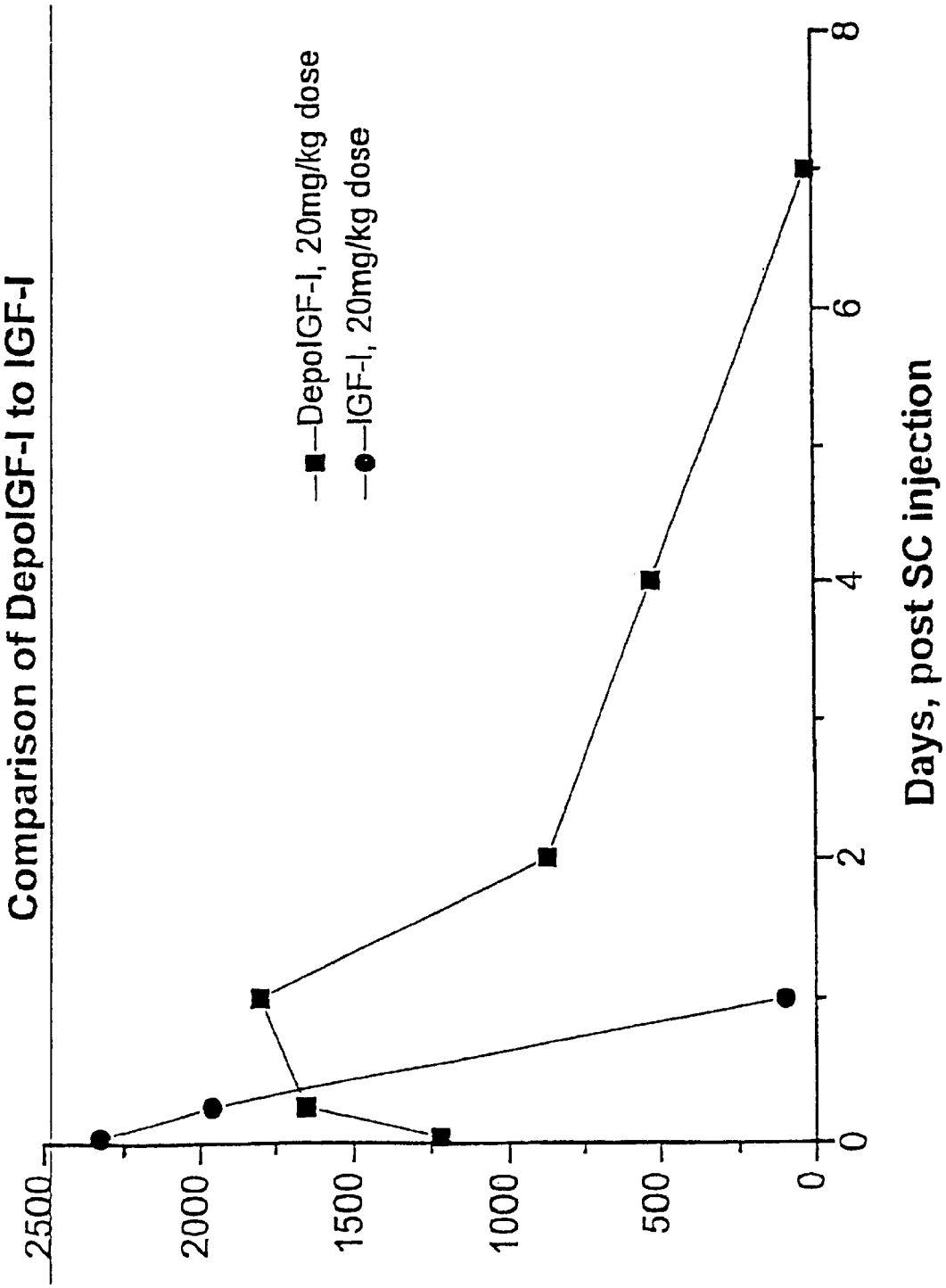
FIG. 6 is a graph showing the in vivo release in serum obtained after subcutaneous injection in rats of IGF-I encapsulated as a low load formulation in MVL. The graph also shows the serum level resulting from an equal dose of free IGF-I. The ordinate shows the percent of IGF-I retained in the particle fraction, and the abscissa shows the days post injection. -●-=IGF-I in MVL, dose of 20 mg/kg; -▲-=free IGF-I, dose of 20 mg/kg.

In-vivo studies. The pharmacokinetic behavior of a low load MVL formulation containing IGF-I was compared to that of unencapsulated IGF-I after subcutaneous injections (lower back) in rats. 20 mg/kg doses of either free IGF-I or a MVL formulation or IGF-I prepared from a stock solution of 5 mg/ml IGF-I was injected into each rat, with 3 rats per group. Sera were collected at various times up to 8 days post injection, and assayed for IGF-I using an IGF-I ELISA kits (DSL-10-5600) (Diagnostic Systems Laboratories (DSL), Webster, Tex.) according to the manufacturer's instructions. The pharmacokinetic parameters were calculated using the WinNonlin program (Scientific Consulting Inc.) and a non-compartmental model. A graph showing results of this study (FIG. 6) indicates that the low load MVL formulation releases a therapeutic level of IGF-I over a 5–7 day period, while free IGF-I is cleared after about 1 day.

While presently preferred embodiments of the invention have been given for the purpose of disclosure, changes may be made therein which are within the spirit of the invention as defined by the scope of the appended claims.

What is claimed is:

1. A multivesicular liposome having multiple non-concentric chambers with membranes distributed as a continuous network throughout, made by a process comprising the steps of:
   a. forming a first aqueous component comprising insulin-like growth factor I (IGF-I) in a concentration range from about 40 mg/mL to about 300 mg/mL, an osmotic excipient and a pH adjusting agent, wherein the aqueous component is calibrated to have an osmolarity in the range from about 5 mOsm and to have a pH in the range from about 2 to about 4.8;
   b. forming a lipid component comprising at least one organic solvent, at least one amphipathic lipid, and a neutral lipid lacking a hydrophilic headgroup;
   c. forming an emulsion from the first aqueous component and the lipid component;
   d. dispersing the emulsion into a second aqueous component to form solvent spherules; and
   e. removing the organic solvent from the solvent spherules to form multivesicular liposomes suspended in the second aqueous component.

2. The liposome of claim 1, wherein the osmotic excipient is selected from the group consisting of glycylglycine, glucose, sucrose, trehalose, succinate, cyclodextrin, arginine, galactose, mannose, maltose, mannitol, glycine, lysine, citrate, sorbitol, dextran, sodium chloride, and combinations thereof.

3. The liposome of claim 1, wherein the osmotic excipient is glycylglycine.

4. The liposome of claim 1, wherein the amphipathic lipid has from about 13 to about 28 carbons in its carbon chain.

5. The liposome of claim 1, wherein the amphipathic lipid has from about 18 to about 22 carbons in its carbon chain.

6. The liposome of claim 5, wherein the amphipathic lipid is 1,2-dierucoyl-sn-glycero-3-phosphocholine.

7. The liposome of claim 5, wherein the amphipathic lipid is 1,2-dioleoyl-sn-glycero-3-phosphocholine.

8. The liposome of claim 1, wherein the pH adjusting agent is citric acid.

9. The liposome according to claim 1, wherein the neutral lipid is selected from the group consisting of triolein, tricaprylin, squalene, and combinations thereof.

10. The liposome according to claim 1, wherein the organic solvent is selected from the group consisting of ethers, hydrocarbons, halogenated hydrocarbons, halogenated ethers, esters, $CHCl_3$(chloroform), Freons, and combinations thereof.

11. A process for producing multivesicular liposomes having multiple non-concentric chambers with membranes distributed as a continuous network throughout, and having insulin-like growth factor I (IGF-I) encapsulated therein, the process comprising the steps of:
   a. forming a first aqueous component comprising insulin-like growth factor I (IGF-I) in a concentration range from about 40 mg/mL to about 300 mg/mL, an osmotic excipient, and a pH adjusting agent, wherein the aqueous component is calibrated to have an osmolarity in the range from about 5 mOsm to about 150 mOsm and to have a pH in the range from about 2 to about 4.8;
   b. forming a lipid component comprising at least one organic solvent, at least one amphipathic lipid, and a neutral lipid lacking a hydrophilic headgroup;
   c. forming an emulsion from the first aqueous component and the lipid component;
   d. dispersing the emulsion into a second aqueous component to form solvent spherules; and
   e. removing the organic solvent from the solvent spherules to form multivesicular liposomes suspended in the second aqueous component.

12. The process of claim 11, wherein the osmotic excipient is sucrose.

13. The process of claim 11, wherein the osmotic excipient is glycylglycine.

14. The process of claim 11, wherein the pH adjusting agent is citric acid.

15. The process of claim 11, wherein the pH adjusting agent is ammonium citrate dibasic.

16. The process of claim 11, wherein the lipid component comprises at least one amphipathic lipid having from about 13 to about 28 carbons in its carbon chain.

17. The process of claim 11, wherein the lipid component comprises at least one amphipathic lipid having from about 18 to about 22 carbons in its carbon chain.

18. The process of claim 11, wherein the osmotic excipient is selected from the group consisting of glycylglycine, glucose, sucrose, trehalose, succinate, cyclodextrin, arginine, galactose, mannose, maltose, mannitol, glycine, lysine, citrate, sorbitol, dextran, sodium chloride, and combinations thereof.

19. The process according to claim 11, wherein the neutral lipid is selected from the group consisting of triolein, tricaprylin, squalene, and combinations thereof.

20. The process of claim 11, wherein the organic solvent is selected from the group consisting of ethers, hydrocarbons, halogenated hydrocarbons, halogenated ethers, esters, $CHCl_3$ (chloroform), Freons, and combinations thereof.

21. A multivesicular liposome having multiple non-concentric chambers with membranes distributed as a continuous network throughout, made by a process comprising the steps of:
   a. forming a first aqueous component comprising insulin-like growth factor I (IGF-I) in a concentration range from about 1 mg/mL to about 33 mg/mL, an osmotic excipient and a pH adjusting agent, to have an osmolarity in the range from about 130 mOsm to about 320 mOsm and to have a pH in the range from about 1 to about 5;
   b. forming a lipid component comprising at least one organic solvent, at least one amphipathic lipid, and a neutral lipid lacking a hydrophilic headgroup;
   c. forming an emulsion from the first aqueous component and the lipid component;
   d. dispersing the emulsion into a second aqueous component to form solvent spherules; and
   e. removing the organic solvent from the solvent spherules to form multivesicular liposomes suspended in the second aqueous component.

22. The process of claim 21, wherein the osmotic excipient is selected from the group consisting of glycylglycine, glucose, sucrose, trehalose, succinate, cyclodextrin, arginine, galactose, mannose, maltose, mannitol, glycine, lysine, citrate, sorbitol, dextran, sodium chloride, and combinations thereof.

23. The process of claim 21, wherein the osmotic excipient is glycylglycine.

24. The liposome of claim 21, wherein the amphipathic lipid has from about 13 to about 28 carbons in its carbon chain.

25. The liposome of claim 21, wherein the amphipathic lipid has from about 18 to about 22 carbons in its carbon chain.

26. The liposome of claim 25, wherein the amphipathic lipid is 1,2-dierucoyl-sn-glycero-3-phosphocholine.

27. The liposome of claim 25, wherein the amphipathic lipid is 1,2-dioleoyl-sn-glycero-3-phosphocholine.

28. The liposome of claim 21, wherein the pH adjusting agent is citric acid.

29. The liposome according to claim 21, wherein the neutral lipid is selected from the group consisting of triolein, tricaprylin, squalene, and combinations thereof.

30. The liposome according to claim 21, wherein the organic solvent is selected from the group consisting of ethers, hydrocarbons, halogenated hydrocarbons, halogenated ethers, esters, $CHCl_3$(chloroform), Freons, and combinations thereof.

31. A process for producing multivesicular liposome having multiple non-concentric chambers with membranes distributed as a continuous network throughout, and having insulin- like growth factor I (IGF-I) encapsulated therein, the process comprising the steps of:
   a. forming a first aqueous component comprising insulin-like growth factor I (IGF-I) in a concentration range from about 1 mg/mL to about 33 mg/mL, an osmotic excipient, and a pH adjusting agent, where the aqueous component is calibrated to have an osmolarity in the range from about 130 mOsm to about 320 mOsm and to have a pH in the range from about 1 to about 5, so as to determine resulting IGF-I load into the liposome;
   b. forming a lipid component comprising at least one organic solvent, at least one amphipathic lipid, and a neutral lipid lacking a hydrophilic headgroup;
   c. forming an emulsion from the first aqueous component and the lipid component;
   d. dispersing the emulsion into a second aqueous component to form solvent spherules; and
   e. removing the organic solvent from the solvent spherules to form multivesicular liposomes suspended in the second aqueous component.

32. The process of claim 31, wherein the osmotic excipient is sucrose.

33. The process of claim 31, wherein the osmotic excipient is glycylglycine.

34. The process of claim 31, wherein the pH adjusting agent is citric acid.

35. The process of claim 31, wherein the pH adjusting agent is ammonium citrate dibasic.

36. The process of claim 31, wherein the lipid component comprises at least one amphipathic lipid having from about 13 to about 28 carbons in its carbon chain.

37. The process of claim 31, wherein the lipid component comprises at least one amphipathic lipid having from about 18 to about 22 carbons in its carbon chain.

38. The process of claim 31, wherein the osmotic excipient is selected from the group consisting of glycylglycine, glucose, sucrose, trehalose, succinate, cyclodextrin, arginine, galactose, mannose, maltose, mannitol, glycine, lysine, citrate, sorbitol, dextran, sodium chloride, and combinations thereof.

39. The liposome according to claim 31, wherein the neutral lipid is selected from the group consisting of triolein, tricaprylin, squalene, and combinations thereof.

40. The liposome according to claim 31, wherein the organic solvent is selected from the group consisting of ethers, hydrocarbons, halogenated hydrocarbons, halogenated ethers, esters, $CHCl_3$(chloroform), Freons, and combinations thereof.

41. A process for producing multivesicular liposome having multiple non-concentric chambers with membranes distributed as a continuous network throughout, and having insulin- like growth factor I (IGF-I) encapsulated therein, the process comprising the steps of:
   a. forming a first aqueous component comprising insulin-like growth factor I (IGF-I) in a concentration range from about 40 mg/mL to about 300 mg/mL, an osmotic excipient, and a pH adjusting agent, where the aqueous component is calibrated to have an osmolarity in the range from about 5 mOsm to about 150 mOsm and to have a pH in the range from about 2 to about 4.8, so as to determine resulting IGF-I load into the liposome;
   b. forming a lipid component comprising at least one organic solvent, at least one amphipathic lipid, and a neutral lipid lacking a hydrophilic headgroup;
   c. forming an emulsion from the first aqueous component and the lipid component;

d. dispersing the emulsion into a second aqueous component to form solvent spherules; and e. removing the organic solvent from the solvent spherules to form multivesicular liposomes suspended in the second aqueous component;

f. repeating steps a–e, except that once the desired IGF-I load is determined, exact amounts of IGF-I, osmotic excipient and pH and adjusting agent are used without further calibration.

42. A process for producing multivesicular liposome having multiple non-concentric chambers with membranes distributed as a continuous network throughout, and having insulin- like growth factor I (IGF-I) encapsulated therein, the process comprising the steps of:

a. forming a first aqueous component comprising insulin-like growth factor I (IGF-I) in a concentration range from about 1 mg/mL to about 33 mg/mL, an osmotic excipient, and a pH adjusting agent, where the aqueous component is calibrated to have an osmolarity in the range from about 130 mOsm to about 320 mOsm and to have a pH in the range from about 1 to about 5; so as to determine resulting IGF-I load into the liposome;

b. forming a lipid component comprising at least one organic solvent, at least one amphipathic lipid, and a neutral lipid lacking a hydrophilic headgroup;

c. forming an emulsion from the first aqueous component and the lipid component;

d. dispersing the emulsion into a second aqueous component to form solvent spherules; and e. removing the organic solvent from the solvent spherules to form multivesicular liposomes suspended in the second aqueous component;

f. repeating steps a–e, except that once the desired IGF-I load is determined, exact amounts of IGF-I, osmotic excipient and pH and adjusting agent are used without further calibration.

* * * * *